United States Patent [19]

Hayward et al.

[11] Patent Number: 4,866,082

[45] Date of Patent: Sep. 12, 1989

[54] INHIBITION OF BONE LOSS BY (−)-N-[[(5-CHLORO-2-BENZOTHIAZOLYL)-THIO]PHENYLACETYL]-L-CYSTEINE

[75] Inventors: Marshall Hayward, Lawrenceville, N.J.; Jean Schmid, Yardley, Pa.

[73] Assignee: American Home Products Corporation, New York, N.Y.

[21] Appl. No.: 178,116

[22] Filed: Apr. 6, 1988

[51] Int. Cl.$^4$ .......................................... A51K 31/425
[52] U.S. Cl. .................................................. 514/367
[58] Field of Search ....................................... 514/367

[56] References Cited

U.S. PATENT DOCUMENTS

| | | | |
|---|---|---|---|
| 4,367,233 | 1/1983 | Clark | 424/270 |
| 4,391,824 | 7/1983 | Siuta | 514/377 |
| 4,567,267 | 1/1986 | Wel | 546/114 |
| 4,599,361 | 7/1986 | Dickens | 514/575 |
| 4,609,667 | 9/1986 | Clark | 514/367 |

OTHER PUBLICATIONS

Delaisse, Bone, 8, 305 (1987).

Primary Examiner—Robert Gerstl
Attorney, Agent, or Firm—Walter Patton

[57] ABSTRACT

A method for modifying the balance between bone production and bone resorption in a host animal by administration of (−)-N-[[(5-chloro-benzothiazolyl)-thio]phenylacetyl]-L-cysteine to inhibit bone loss.

3 Claims, No Drawings

INHIBITION OF BONE LOSS BY (−)-N-[[(5-CHLORO-2-BENZOTHIAZOLYL)THIO]-PHENYLACETYL]-L-CYSTEINE

This invention relates to a process for modifying the balance between bone production and bone resorption in a host animal, including man, and more specifically to the use f (−)-N-[[(5-chloro-2-benzothiazolyl)thio]-phenylacetyl]-L-cysteine for the inhibition of bone loss.

BACKGROUND OF THE INVENTION

Osteoporosis is a skeletal disorder which is evidenced by a decrease in bone density throughout the body. In fact, both the bone mineral (calcium phosphate called "hydroxyapatite") and the matrix (major protein called "collagen") are slowly lost. This condition may begin to occur in humans as early as age 30. In general, the process is more rapid in postmenopausal women than in men. However, after age 80 there is no sex difference in the incidence of osteoporosis. In the course of 10 to 20 years of bone loss there may be symptoms of back pain and X-ray evidence of deformation of the back bine. At older ages, the brittleness of the bones becomes evident by the ease in which the proximal femur ("hip") fractures. Osteoporosis is the most common cause of fractures in people over age 45.

Although the cause of osteoporosis is poorly understood, it is believed that there is an imbalance between bone production and bone resorption (bone breakdown). Bone remains a dynamic tissue throughout the life of an animal. That is, new bone is continuously being formed and old bone is continuously being resorbed. However, in animals suffering from an osteoporotic condition, net bone resorption exceeds bone formation.

A survey indicates that in the United States there may be fifteen to twenty million afflicted with osteoporosis. W. A. Peck (Chairman), NIH Osteoporosis Consensus Conference, J. Am. Med. Assoc. 10, 252: 799–802 (1984). Various types of osteoporosis are designated according to special conditions believed to be causative: senile (aging); post-menopausal (female loss of estrogenesis); disuse (chronic immobilization); steroid (long term steroid treatment as in arthritis). Osteoporosis may also be manifested in dental problems since the mandible appears to lose mass more rapidly than any other bone. Thus, periodontal disease involving a loosening of the adult teeth may be an early sign of osteoporosis.

The mechanism of bone loss is at present poorly understood. Moreover, the present methods of treatment are generally unsatisfactory. These include anabolic agents, various drugs containing phosphorous, Vitamin D, calcium salts, fluorides and calcitonin.

Estrogen replacement therapy has been the therapy of choice for osteoporosis in post-menopausal women.

Physical therapy is another method currently used to treat osteoporosis since immobilization can cause osteoporosis at any age. Thus, many physicians believe that exercise and physical therapy can prevent the progression of the disease in elderly patients. However, physical therapy can be harmful for patients with fractures and, moreover, overstrenuous exercise can cause fractures in patients with severe osteoporosis.

Other treatments include the administration of a fluoride salt such as sodium fluoride which has been shown to promote bone growth clinically, apparently by stimulating collagen synthesis. However, a serious side effect is poorly calcified, irregular bone growth. Another treatment involves infusion of calcium and Vitamin D to counteract the deficiency of calcium or impaired absorption of calcium which is symptomatic in some elderly patients. There is, however, no evidence that a higher intake of calcium will prevent osteoporosis or increase bone mass and it could increase urinary calcium excretion.

The most promising therapeutic approach to the treatment of osteoporosis is the administration of agents which have been designed to modify the balance between the rate of bone production and the rate of bone resorption in such a manner that the ratio of the former to the latter is increased, resulting in no net bone loss. After the previously occurred bone losses have been restored, a steady state is reached where the rate of bone production and rate of bone resorption are equal. Such a modification may be effected by stimulating the physiological mechanism of bone deposition, i.e., bone formation, or by retarding the mechanism of bone resorption, or both. Drugs presently in use or in the experimental stages for accomplishing these purposes include inorganic phosphate type drugs, calcitonin and mithramycin. However, all of these drugs suffer serious drawbacks.

Mithramycin, an antibiotic, has anti-tumor activity together with hypocalcemic activity, effecting a lowering of serum calcium which in turn is believed to be indicative of a decrease in the relative rate of bone resorption—i.e., bone resorption relative to bone production. Side effects, however, include renal and hepatic toxicity as well as nausea. Likewise, the organic phosphates (called "phosphonates") have side effects which include extraskeletal calcification, hypotension and renal failure. Calcitonin presents an immunological problem because it is derived from a non-human source. Thus, none of the foregoing agents are at present suitable for use alone in the treatment of osteoporosis.

SUMMARY OF THE INVENTION

It is an object of this invention to provide a method wherein a host animal, including man, suffering from osteoporosis is treated in order to modify the balance between the rates of bone deposition and bone resorption in said host animal whereby the ratio of the latter to the former is reduced.

It is another object of this invention to provide a process for the treatment of a host animal in order to prevent the deterioration of existing healthy bone tissues in said host animal.

It is a further object of this invention to provide a process for the treatment of periodontal disease.

These and other objects are achieved by the practice of this invention which, briefly, comprises administering to a host animal, including man, the compound (−)-N-[[(5-chloro-2-benzothiazolyl)thio]phenylacetyl]-L-cysteine having the chemical structure (I)

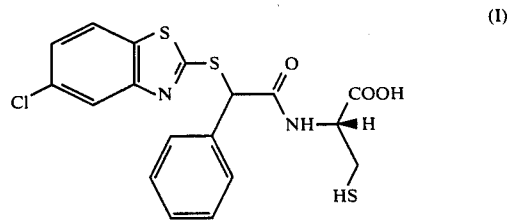

It is another object of this invention to provide an improved process for the production of (—)-N-[[(5-chloro-2-benzothiazolyl)thio]phenylacetyl]-L-cysteine.

(—)-N-[[5-Chloro-2-benzothiazolyl)thio]-phenylacetyl]-L-cysteine has been demonstrated to possess inhibitory activity regarding the collagen proteolytic enzyme, collagenase in U.S. Pat. No. 4,367,233, and its preparation and its use in arthritic disease is disclosed in U.S. Pat. No. 4,567,267, both hereby incorporated herein by reference in their entirety.

DETAILED DESCRIPTION OF THE INVENTION

Collagen is the major constituent of bone matrix, and is degraded during the process of bone resorption and leads to the subsequent development of osteoporosis. The resent invention provides a method for the treatment of a host animal in order to modify the balance between the rate of bone resorption and the rate of bone deposition in said host animal whereby the ratio of said rate of bone resorption to said rate of bone deposition is reduced, comprising administering to said host animal an amount, sufficient to modify said balance and reduce said ration, of (—)-N-[[(5-chloro-2-benzothiazolyl)thio]phenylacetyl]-L-cysteine. (—)-N-[[(5-Chloro-2-benzothiazolyl)thio]phenylacetyl]-L-cysteine would be administered to humans at a daily dose of 200 mg to 1200 mg.

The advantageous effects of (—)-N-[[(5-chloro-2-benzothiazolyl)thio]phenylacetyl]-L-cysteine in preventing bone loss in accordance with the present invention are demonstrated by the following experimental results.

(—)-N-[[(5-Chloro-2-benzothiazolyl)thio]-phenylacetyl]-L-cysteine was examined for its effects in two distinct rodent models of bone demineralization. Significant bone sparing activity was observed with (—)-N-[[(5-chloro-2-benzothiazolyl)thio]phenylacetyl]-L-cysteine at 50 mg/kg i.p. in an immobilization dependent model of osteopenia in the rat femur. In a model of cancellous bone loss performed in ovariectomized rats, significant retention of bone resulted from the treatment of rats with (—)-N-[[(5-chloro-2-benzothiazolyl)thio]phenylacetyl]-L-cysteine at doses of 20 mg/kg i.p. over a 6 week period.

The following Examples show the preparation and testing of the compound used in this invention.

EXAMPLE 1

(—)-N-[[(5-Chloro-2-benzothiazolyl)thio]-phenylacetyl]-L-cysteine (Diastereoisomer B)

(Step 1) Preparation of α-(5-Chlorobenzothiazol-2-ylthio)benzene Acetic Acid

To a solution of 5-chloro-2-mercaptobenzothiazole (38 g, 0.188 mol) in methylene chloride (750 mL) was added α-bromophenylacetic acid (38 g, 0.177 L mol) and triethylamine (38.5 g, 53 mL, 0.38 mol). The mixture was heated to reflux overnight. The clear solution was evaporated in vacuo and the residue was taken up in ethyl acetate, washed with dilute hydrochloric acid solution, then with water and finally dried over magnesium sulfate and filtered. The filtrate was concentrated in vacuo to a small volume and treated with n-hexane whereby the product crystallized out. Filtration yielded the product as a beige crystalline compound (41 g, 70%), m.p. 184°–185° C.

NMR (DMSO-d$_6$, 400 MHz): δ 5.79 (s, 1H), 7.35–7.56 (m, 6H, Ar—H), 7.92 (d, J=2 Hz, 1H, Ar—H), 8.03 (d, J=8.6 Hz, 1H, Ar—H)

(Step 2) Preparation of 6-Chloro-2-phenylthiazolo[2,3-b]benzothiazol-3(2H)-one Mesoionic Didehydro Derivative α-(5-Chlorobenziothiazol-2-ylthio)benzene acetic acid (39 g, 0.116 mol) was suspended in methylene chloride (3.5 L) and the mixture was heated to gentle reflux in the presence of acetic anhydride (50 mL). The solids gradually dissolved, the solution turned reddish. After heating for two days the solution was concentrated in vacuo to ~250 mL and the suspension was diluted with n-hexane (300 mL), filtered and washed with methylene chloride/hexane (1:3, 100 mL), to afford an orange, crystalline compound (32.8 g, 89%), m.p. 211°–212° C. (dec.).

NMR (DMSO-d$_6$, 400 MHz): δ 7.02 (t, J=8 Hz, 1H, Ar—H), 7.3 (t, J=8 Hz, 2H, Ar—H), 7.7 (d, J=8 Hz, 1H, Ar—H), 7.82 (d, J=8 Hz, 2H, Ar—H), 8.25 (d, J=8 Hz, 1H, Ar—H), 9.0 (s, 1H, Ar—H)

(Step 3) Preparation of (—)-N-[[(5-Chloro-2-benzothiazolyl)thio]-phenylacetyl]-L-cysteine (Diastereoisomer B)

6-Chloro-2-phenylthiozolo[2,3-b]benzothiazol-3(2H)-one mesoionic didehydro derivative (92 g, 0.282 mol), L-(—)-cysteine (70.2 g, 0.579 mol) and triethylamine (135 mL) were suspended in methylene chloride (1.53 L) and the mixture was stirred vigorously under nitrogen at ambient temperature for two days. The orange colored suuspension changed to a pale yellow mixture. Some insoluble material (excessive L-cysteine) was filtered off and the clear filtrate was washed with dilute hydrochloric acid solution, water and then dried over magnesium sulfate. The foamy residue left after solvent removal was triturated twice with a mixture of ether-hexane and crystalline diastereoisomer A was collected by filtration.

The clear filtrate containing diastereoisomer B was evaporated to dryness. The resulting solid residue was crystallized from ethanol and recrystallized from a mixture of ethanol-methylene chloride-hexane to yield the pure diastereoisomer B as a white crystalline compound (17.2 g, 14%), m.p. 158°–160° C.

Diastereoisomer B

NMR (DMSO-d$_6$, 400 MHz): δ 2.03 (t, J=8.5 Hz, 1H, S—H), 2.71–2.78 (m, 2H, CH$_2$), 4.37–4.42 (m, 1H, NH—CH), 5.96 (s, 1H, S—CH—Ar), 7.30–7.42 (m, 4H, Ar—H), 7.63 (m, 2H, Ar—H), 7.89 (d, J=2 Hz; 1H, Ar—H), 8.03 (d, J=8.6 Hz, 1H, Ar—H), 9.04 (d, J=7.9 Hz, 1H, NH)

IR (cm$^{-1}$): 3780(s), 2500–3600(b), 1710(s), 1640(s)

Anal. Calcd.: C, 49.26; H, 3.44; N, 6.38%, Found: C, 49.15; H, 3.24; N, 6.33, [α]$_D^{25}$ in MeOH: −166.83°.

EXAMPLE 2

N-[[(5-Chloro-2-benzothiazolyl)thio]phenylacetyl]-L-cysteine (Diastereoisomer A)

6-Chloro-2-phenylthiozolo[2,3-b]benzothiazol-3(2H)-one mesoionic didehydro derivative (30 g, 0.094 mol), L-(—)-cysteine (22.9 g, 0.189 mol) and triethylamine (31.9 g, 44 mL, 0.315 mol) were suspended in methylene chloride (500 mL) and the mixture was stirred vigorously under nitrogen at ambient temperature overnight. The orange colored suspension changed to a pale yellow mixture. Some insoluble material (excessive L-cysteine) was filtered off and the clear filtrate was washed with dilute hydrochloric acid solution, water and then dried over magnesium sulfate. After solvent removal, the pale yellow solids (38.5 g, 1:1 mixture of diastereoisomers by NMR) were dissolved in ethanol (100 mL) methylene chloride (250 mL) and the clear solution was concentrated in vacuo to a small volume. Upon addition of ether (200 mL) the crystalline isomer A was precipitated then filtered and washed with ether (100 mL) to yield an off-white product (11.1 g). This product was dissolved in an ethanol/methylene chloride mixture, then concentrated in vacuo to a small volume and treated with ether to afford a white crystalline compound (7.0 g, 19%), m.p. 164°–165° C.

Diastereoisomer A

NMR (DMSO-d$_6$, 400 MHz): δ 2.42 (t, J=8.5 Hz, 1H, S—H), 2.8–2.89 (m, 2H, —CH$_2$), 4.44–4.46 (m, 1H, NH—CH), 5.96 (s, 1H, S—CH—Ar), 7.32–7.44 (m, 4H, Ar—H), 7.6 (d, J=6.9 Hz, 2H, Ar—H), 7.9 (d, J=2 Hz, 1H, Ar—H), 8.04 (d, J=8.5 Hz, 1H, Ar—H), 8.98 (d, J=7.8 Hz, 1H, —NH).

IR (CM$^{-1}$): 3400–2500(br) 1720(s), 1665(s).

MS: m/e 439 (M+), 202.

Anal. Calcd.: C, 49.25; H, 3.44; N, 6.38%, Found: C, 49.18; H, 3.43; N, 6.36%, [α]$_D^{25}$ in MeOH: +139.76°.

EXAMPLE 3

Immobilization Dependent Bone Loss in the Rat Femur

This assay was performed according to a modification of a procedure described by A. D. Kenny, "Role of Carbonic Anhydrase in Bone: Partial Inhibition of Disuse Atrophy of Bone by Parenteral Acetazolamide," Calcif. Tissue Int., 37, 126–133 (1985).

Bone mass was determined in contralateral femora from ovariectomized rats which had been subjected to unilateral sciatic nerve severence. After sciatic neurotomy the rats were treated with (−)-N-[[(5-chloro-2-benzothiazolyl)thio]phenylactyl]-L-cysteine (50 mg/kg/day i.p., 5x/week) for a total of 4 weeks. Rats were euthanized, then femora were excised, debrided of soft tissue, then dehydrated. After drying, the mass of each pair of femora was determined by weighing. The bone mass data are summarized in Table 1, which demonstrates the significant retention of bone in immobilized femora in rats treated with (−)-N-[[(5-chloro-2-benzothiazolyl)thio]phenylacetyl]-L-cysteine relative to vehicle treated control rat femora.

TABLE 1

Effect of (−)-N—[[(5-Chloro-2-benzothiazolyl)thio]phenylacetyl]-L-cysteine on Bone Loss in Immobilization Dependent Osteoporosis

| Treatment | (n) | Dehydrated Femur mass, mg, Mean ± SEM | | | % Change in Femur mass |
|---|---|---|---|---|---|
| | | Control Femur | Immobilized Femur | Difference | |
| Vehicle | (9) | 471.1 ± 7.8 | 419.2 ± 9.8 | 51.9 ± 4.7 | 11.02 |
| (−)-N—[[(5-Chloro-2-benzothiazolyl)thio]phenylacetyl]-L-cysteine 50 mg/kg i.p. | (9) | 468.7 ± 13.1 | 432.4 ± 11.8 | 36.2 ± 4.8* | 7.8* |

*p < 0.05 vs Vehicle Difference

EXAMPLE 4

Ovariectomy Dependent Cancellous Bone Loss in the Tibia

This assay was performed in an experimental model based on the work described by T. J. Wronski, P. L. Lowry, C. C. Walsh and L. A. Ignaszewski, "Skeletal Alteration in Ovariectomized Rats," Calcif. Tissue Int., 37, 324–238 (1985).

Cancellous bone content was determined in the proximal metaphysis of rats which had been subjected to variectomy for a period of 8 weeks. Two weeks after ovariectomy, treatment with (−)-N-[[(5-chloro-2-benzothiazolyl)thio]phenylacetyl]-L-cysteine (20 mg/kg/day, i.p., 5 mg/kg/day i.p. or an equivalent injection of vehicle) was initiated and continued for 6 weeks. Animals received treatment 5 days on/2 days off per week. Rats were euthanized, then tibia were excised, fixed, and processed for histological assessment. The bone mineral present within the proximal metaphysis was quantified with a computer-assisted image analysis system. The region of bone mineral quantitation in the proximal tibia selected for cancellous bone content evaluation are the primary and secondary spongiosa. To select and standardize this area for evaluation, the epiphyseal growth plate-metaphyseal junction is oriented parallel to the abscissa of the digitizing screen. Bone elements 1.7 mm (secondary spongiosa) and 0.2 mm (primary spongiosa) from the growth plate and equidistant from the flanking cortical elements are then quantified as described above. The total area evaluated is 2.3 mm wide and 1.45 mm deep, constituting a 3.34 mm$^2$ area and summary data are compiled in Table 2. Treatment of rats with (−)-N-[[(5-chloro-2-benzothiazolyl)thio]phenylacetyl]-L-cysteine at 20 mg/kg demonstrated significant bone mineral retention relative to vehicle treated control animals.

TABLE 2

Effect of (−)-N—[[(5-Chloro-2-benzothiazolyl)thio]phenylacetyl]-L-cysteine on Bone Loss as Judged by Histological Assessment of Cancellous Bone Within the Proximal Tibia in Ovariectomy Dependent Osteopenia in Rats

| Treatment | (n) | Bone Mineral Content, as Area % Mineralized Tissue Mean ± SEM | |
|---|---|---|---|
| | | Primary Spongiosa | Secondary Spongiosa |
| Vehicle | (9) | 11.2 ± 0.8 | 4.1 ± 0.7 |

TABLE 2-continued

Effect of (—)-N—[[(5-Chloro-2-benzothiazolyl)thio]phenylacetyl]-L-cysteine on Bone Loss as Judged by Histological Assessment of Cancellous Bone Within the Proximal Tibia in Ovariectomy Dependent Osteopenia in Rats

| Treatment | (n) | Bone Mineral Content, as Area % Mineralized Tissue Mean ± SEM | |
|---|---|---|---|
| | | Primary Spongiosa | Secondary Spongiosa |
| (—)-N—[[(5-Chloro-2-benzothiazolyl)thio]phenylacetyl]-L-cysteine 20 mg/kg i.p. | (8) | 13.3 ± 0.8 | 8.0 ± 1.1* |

*$p < 0.01$ vs Vehicle Group

The administration of (—)-N-[[(5-chloro-2-benzothiazolyl)thio]phenylacetyl]-L-cysteine in accordance with this invention can be supplemental to other regimens for the treatment of osteoporosis or periodontitis. For example, the administration of (—)-N-[[(5-chloro-2-benzothiazolyl)thio]phenylacetyl]-L-cysteine can be supplemental to the 600 mg to 1200 mg daily intake of calcium as calcium phosphate or calcium carbonate. Also, the administration of (—)-N-[[(5-chloro-2-benzothiazolyl)thio]phenylacetyl]-L-cysteine can be supplemental to estrogen replacement therapy such as 0.625 mg daily of conjugated equine estrogen.

We claim:

1. A method for the treatment of a host animal in order to modify the balance between the rate of bone resorption and the rate of bone formation in said host animal whereby the ratio of said rate of bone resorption to said rate of bone formation is reduced, comprising administering to said host animal an amount of (—)-N-[[(5-chloro-2-benzothiazolyl)thio]phenylacetyl]-L-cysteine sufficient to modify said balance and reduce said ratio.

2. The method of claim 1 wherein the (—)-N-[[(5-chloro-2-benzothiazolyl)thio]phenylacetyl]-L-cysteine is administered at a daily dose ranging from 200 mg to 1200 mg.

3. The method of claim 2 wherein the (—)-N-[[(5-chloro-2-benzothiazolyl)thio]phenylacetyl]-L-cysteine is administered at a dose of 500 mg twice daily for a total daily dose of 1000 mg.

* * * * *